(12) United States Patent
Bessonov et al.

(10) Patent No.: US 11,602,732 B2
(45) Date of Patent: Mar. 14, 2023

(54) POLYMERIC SORBENT, PREPARATION AND USE THEREOF

(71) Applicant: EFFERON GMBH, Frankfurt am Main (DE)

(72) Inventors: Ivan Viktorovich Bessonov, Moscow (RU); Alexey Sergeevich Morozov, Moscow (RU); Maria Nikolaevna Kopitsyna, Moscow (RU)

(73) Assignee: EFFERON GMBH, Frankfurt am Main (DE)

( * ) Notice: Subject to any disclaimer, the term of this patent is extended or adjusted under 35 U.S.C. 154(b) by 491 days.

(21) Appl. No.: 16/616,403

(22) PCT Filed: May 17, 2018

(86) PCT No.: PCT/RU2018/050052
§ 371 (c)(1),
(2) Date: Nov. 22, 2019

(87) PCT Pub. No.: WO2018/217137
PCT Pub. Date: Nov. 29, 2018

(65) Prior Publication Data
US 2020/0139348 A1    May 7, 2020

(30) Foreign Application Priority Data
May 23, 2017 (RU) ................ RU2017117852

(51) Int. Cl.
| | | |
|---|---|---|
| B01J 20/32 | (2006.01) | |
| A61M 1/36 | (2006.01) | |
| B01J 20/26 | (2006.01) | |
| B01J 20/28 | (2006.01) | |

(52) U.S. Cl.
CPC .......... *B01J 20/327* (2013.01); *A61M 1/3679* (2013.01); *B01J 20/267* (2013.01); *B01J 20/28064* (2013.01); *B01J 20/28066* (2013.01); *B01J 20/3274* (2013.01); *B01J 20/3276* (2013.01); *B01J 2220/445* (2013.01); *B01J 2220/4825* (2013.01); *B01J 2220/50* (2013.01)

(58) Field of Classification Search
CPC ........ B01J 20/32; B01J 20/327; B01J 20/267; B01J 20/28064; B01J 20/28066; B01J 20/3274; B01J 20/3276; B01J 2220/445; B01J 2220/4825; B01J 2220/50
USPC ...................................................... 502/402
See application file for complete search history.

(56) References Cited

U.S. PATENT DOCUMENTS

| | | |
|---|---|---|
| 3,729,457 A | 4/1973 | Davankov et al. |
| 4,263,407 A | 4/1981 | Reed, Jr. |
| 5,288,307 A | 2/1994 | Goltz et al. |
| 5,416,124 A | 5/1995 | Stringfield |
| 5,683,800 A | 11/1997 | Stringfield et al. |
| 5,773,384 A | 6/1998 | Davankov et al. |
| 6,114,466 A | 9/2000 | Davankov et al. |
| 6,527,735 B1 | 3/2003 | Davankov et al. |
| 2001/0006160 A1 | 7/2001 | Niklas et al. |
| 2002/0146413 A1 | 10/2002 | Brady et al. |
| 2003/0027879 A1 | 2/2003 | Davankov et al. |
| 2005/0061742 A1 | 3/2005 | Brady et al. |
| 2012/0238441 A1 | 9/2012 | Young et al. |
| 2013/0105396 A1 | 5/2013 | Falkenhagen et al. |
| 2015/0157779 A1 | 6/2015 | Falkenhagen et al. |

FOREIGN PATENT DOCUMENTS

| | | |
|---|---|---|
| CN | 103221079 A | 7/2013 |
| CN | 104024291 A | 9/2014 |
| CN | 105037626 A | 11/2015 |
| EP | 2319618 | 5/2011 |
| JP | S55-18297 A | 2/1980 |
| JP | H10-502107 A | 2/1998 |
| JP | 2001-261983 A | 9/2001 |
| JP | 2001-525200 A | 12/2001 |
| JP | 2005-514127 A | 5/2005 |
| JP | 2013-537923 A | 10/2013 |
| RU | 1781235 | 12/1992 |
| RU | 1455654 | 3/1993 |
| RU | 1804000 | 6/1995 |
| RU | 2089283 | 9/1997 |
| RU | 2590225 | 7/2016 |
| WO | 95/35327 A1 | 12/1995 |
| WO | 97/35660 | 10/1997 |
| WO | 99/06098 A1 | 2/1999 |
| WO | 03/057356 A2 | 7/2003 |
| WO | 03/097112 | 11/2003 |
| WO | 2012/033522 | 3/2012 |
| WO | 2013098045 A1 | 7/2013 |

OTHER PUBLICATIONS

Notice of Reasons for Refusal dated Apr. 4, 2022, directed to JP Application No. 2020-516368; 19 pages.
Office Action dated Feb. 15, 2022, directed to CO Application No. NC2019/0012780; 18 pages.
Examination Report dated May 6, 2021, directed to IN Application No. 201917045770; 10 pages.
Honoré et al. (Jan. 2019). "Hemoadsorption therapy in the critically ill:solid base but clinical haze," Annals of Intensive Care 9(22): 2 pages.

(Continued)

*Primary Examiner* — Edward M Johnson
(74) *Attorney, Agent, or Firm* — Banner & Witcoff, Ltd.

(57) ABSTRACT

Polymer sorbents selectively remove cytokines and bacterial endotoxins from whole blood and other body liquids, in particular blood plasma, lymph etc., as well as from aqueous protein solutions and aqueous organic compound solutions, also containing inorganic salts. The sorbent is able to remove both cytokines and bacterial endotoxins, improve selectivity of the polymer sorbents in respect to the compounds as well as provide a simple and effective method of producing said sorbent.

8 Claims, No Drawings

(56) References Cited

OTHER PUBLICATIONS

Kaar et al. (Jan. 2020). "Efficacy of HA330 Hemoperfusion Adsorbent in Patients Followed in the Intensive Care Unit for Septic Shock and Acute Kidney Injury and Treated with Continuous Venovenous Hemodiafiltration as Renal Replacement Therapy," Blood Purification 49: 448-456.

(2006). "Toraymyxin PMX-20R Extracorpal Cartridge Hemoperfusion: Instructions for Use," Toray Medical Co., Ltd.: 16 pages.

Anspach. (2001). "Endotoxin Removal by Affinity Sorbents," Journal of Biochemical and Biophysical Methods 49: 665-681.

Gauthier et al. (2009). "Synthesis of Functional Polymers by Post-Polymerization Modification," Angewandte Chemie 48: 48-58.

Günay et al. (2013) "Standing on the Shoulders of Hermann Staudinger: Post-polymerization Modification from Past to Present," Journal of Polymer Science Part A: Polymer Chemistry 51: 1-28.

Hirayama et al. (2002). "Chromatographic Removal of Endotoxin from Protein Solutions by Polymer Particles," Journal of Chromatography B. 781: 419-432.

International Search Report and Written Opinion dated Oct. 9, 2018, directed to International Application No. PCT/RU2018/050052; 14 pages.

Kireev. (1992). "High-Molecular Connection," Vysshaya Shkola: Moscow, 22 pages.

Morozov et al. (2016). "A Selective Sorbent for Removing Bacterial Endotoxins from Blood," Russian Journal of Physical Chemistry A 90(12): 1876-1882.

Nagaki et al. (Jan. 1991). "Removal of Endotoxin and Cytokines by Adsorbents and the Effect of Plasma Protein Binding," International Journal of Artificial Organs 14(1): 1 page.

Petit et al. (1977). Synthesis of Copper(II) Complexes of Asymmetric Resins Prepared by Attachment of $\alpha$-Amino Acids to Cross-linked Polystyrene, Journal of Applied Polymer Science 21: 2589-2596.

Teramoto et al. (2002). "Amidomethylation of Vinyl Aromatic Polymers with N-Methylol-2-chloroacetamide," Polymer Journal 34(5): 363-369.

Xiao et al. (Aug. 2014). "Cationic Polystyrene Spheres for Removal of Anionic Contaminants in White Water of Papermaking," Journal of Applied Polymer Science: 6 pages.

Anirudhan et al., Selective adsorption of hemoglobin using polymer-grafted magnetite nanocellulose composite, Carbohydrate Polymers 93, pp. 518-527 (2013).

Ruokolainen et al., Critical Interaction Strength for Surfactant-Induced Mesomorphic Structures in Polymer-Surfactant Systems, Macromolecules, 29, pp. 6621-6628 (1996).

POLYMERIC SORBENT, PREPARATION AND USE THEREOF

CROSS-REFERENCE TO RELATED APPLICATIONS

This application is a U.S. national stage patent application of International Patent Application No. PCT/RU2018/050052, filed May 17, 2018, which claims the priority of Russian Application No. 2017117852 filed May 23, 2017, the entire contents of each of which are incorporated herein by reference.

FIELD OF THE INVENTION

This invention relates to polymer chemistry, in particular, to sorption materials designed for selective cytokine and bacterial endotoxin removal from whole blood and other body fluids, in particular, blood plasma, lymph, etc., as well as from aqueous protein solutions and aqueous organic compound solutions, also containing inorganic salts, as well as to method of producing such sorption materials and method of using such sorption materials.

BACKGROUND OF THE INVENTION

Sepsis is a life-threatening condition that is caused by a severe infection. In most cases, sepsis is a complication and a terminal stage of a major injury, a severe burn, a purulent process or a similar condition. The inflammatory response is regulated by complex immune pathways of pro-inflammatory and anti-inflammatory mediators and adjuvants. Known representatives of these pathways include, but are not limited to the following list of substances: cytokines, nitrous oxide, thromboxanes, leukotrienes, platelet-activating factor, prostaglandins, kinins, complement factors, monokines, chemokines, interferons, proteases, metabolites of arachidonic acid, prostacyclins, (3-endorphins, anandamide, histamine, bradykinin and serotonin.

Bacterial endotoxins (lipopolysaccharides), toll-like receptor 4 ligands located on immune cells are primary triggers in cytokine synthesis. A small number of original factors (immune response triggers) increases the cytokine concentration, which initiates a complex immune pathway. This pathway results in damage to healthy tissues and organs due to multiple thrombosis (multiple organ dysfunction syndrome) and death.

Uncontrolled and delocalized inflammatory process leads to severe damage to tissues, organs and systems and may result in death. Above-mentioned cytokines are a class of proteins produced by macrophages, monocytes and lymphocytes in response to a bacterial infection. Cytokines are able to promote their own synthesis and production of other cytokines using a range of different cells. This condition is termed "cytokine release syndrome" (also "cytokine storm"). Cytokines are normally present in blood in very low concentrations. Sepsis leads to cytokine overproduction.

Lipopolysaccharides are able to induce an inflammatory response in as low concentrations as $~10^{-11}$ g/L. Lipopolysaccharides are surface-active species and form micelles and aggregates of variable composition in aqueous solutions. These supramolecular structures can include blood cells and blood plasma proteins, as well as metal cations. Due to this fact, decreasing endotoxin concentration in whole blood below a pathogenic level is a very complex problem.

Hemosorption is a therapy which directly extracts toxic substances from the patient's blood or blood plasma. Blood is collected from a vein, passed through a sorption column and returned to the circulatory system. This method is widely applied to treat sepsis, intoxication and shock.

Two types of sorbents are currently used for hemosorption in case of sepsis. Type 1 are non-specific sorbents, activated carbons, porous polymeric materials. They have a developed porous structure and able to bind a wide range of toxic substances, allowing to simultaneously remove various exogenous and endogenous organic substances from blood. Type 2 are specific selective sorbents, produced by immobilizing organic molecules with specific structure (ligands) on inert substrates. Ligands are specific to a particular toxic agents. They can be biologic (antibodies) or synthetic.

Prior art includes a number of sources related to type 1 and type 2 sorbents.

In particular, a patent WO2003097112 from prior art suggests a method of removing bacterial endotoxins (lipopolysaccharides, LPS) from aqueous solutions and body fluids using LPS-binding ligands that have been covalently immobilized on carriers.

According to WO2003097112, weakly branched organic oligoamines of various structure are used as ligands. At the same time, the patent WO2003097112 does not disclose a method to produce such ligands and does not list examples that would demonstrate the sorption activity of sorbents containing such ligands.

According to WO2003097112, insoluble biopolymer particles, such as agarose, dextran, cellulose or starch, insoluble synthetic polymer particles, such as polystyrene, polyacrylamide, polyvinyl alcohol, as well as inorganic materials, such as glass, aluminium oxide, silicon oxide and other metal oxides.

According to WO2003097112, the sorption materials and the method of use thereof, disclosed in WO2003097112, are effective only for bacterial endotoxin removal from body fluids.

However, removing only bacterial endotoxins from blood is not an effective therapy choice in a case of sepsis, because the development of a systemic inflammatory response is affected by a wide spectrum of cytokines that regulate the inflammatory response. Moreover, the sorption materials suggested by WO2003097112 do not fullfill the biocompatibility requirements, are not meant to contact whole blood in the course of hemosorption.

Another patent, US2002146413, describes a method of organism detoxification using double-porosity polymer sorbents based on polydivinylbenzene polymers.

However, this method has several disadvantages. The surface of hemosorbent used in this method is hydrophobic, has low biocompatibility and causes blood to coagulate on contact, which can lead to clot formation later. To increase biocompatibility, the authors of US2002146413 suggest to make these particles hydrophilic using polyvinylpyrrolidone or polyethylene glycol. However, the addition of a new sorption material production stage introduces new technological issues. Moreover, this treatment reduces the available pore volume and, as a result, decreases the sorption capacity of the material. No exact data for the sorption capacity were disclosed in US2002146413.

Prior art also includes a patent US20050061742A1, which suggests a method of organism detoxification using polymer sorbents based on double-porosity hypercrosslinked polystyrene. Sorbents disclosed in US20050061742A1, methods of production thereof and methods of use thereof are the closest equivalents of the inventions we claim.

This document claims a sorption material based on hypercrosslinked polystyrene with a developed porous structure, high sorption capacity and excellent hemocompatibility. Materials of this kind have been first described by V. A. Davankov and M. P. Tsyurupa in 1969 (Davankov, et al., U.S. Pat. No. 3,729,457, April 1973; Reactive Polymers, 13, 27-42, 1990). Polymers of this kind are obtained by complete cross-linking of polystyrene chains with bifunctional rigid cross-linking agents in the presence of thermodynamically suitable solvent. The precursor polystyrene should be soluble or swell in this solvent. The final product is a polymer with a developed porous structure (800 to 1000 $m^2/g$) and is able to swell in any solvents, including water.

The sorbent disclosed in US20050061742A1 is based on a polymer produced by polymerizing alkene monomers, such as styrene and divinylbenzene, in a two-phase system of water and organic solvent in the presence of a porogen (for example, cyclohexane, cyclohexanone and other θ-solvents for polystyrene or θ-solvents that are a mixture of suitable solvents for polystyrene, such as toluene, benzene, dichloroethene, dichloropropene, tetrachloroethylene, dioxane, dichlorocarbene, and of substances unable to dissolve polystyrene, such as aliphatic hydrocarbons, alcohols, acids) and in the presence of a radical polymerization initiator (for example, benzoyl peroxide) while mixing at 100 to 500 rpm rate. Polymerization in this mode ("suspension polymerization") leads to formation of regular spherical polymer particles with a porous structure.

After this, polystyrene chains are cross-linked in a preswelled state in excess of bifunctional electrophilic cross-linking agents, which leads to the formation of rigid bridges between closely located solvated polystyrene polymer chains due to Friedel-Crafts reaction mechanism.

According to US20050061742A1, polymer cross-linking is carried out in the absence of any modificators, so that the hypercrosslinked structure is distributed evenly across the volume of polymer sorbent beads. The sorbent disclosed in US20050061742A1 is characterized by good hemocompatibility and high sorption capacity with respect to protein molecules, including cytokines with molecular masses in the range of 8 to 29 kDa. At the same time, the bacterial endotoxin removal efficiency of this sorbent is limited. (Nagaki M, Hughes R D, Lau J Y, Williams R, Removal of endotoxin and cytokines by adsorbents and the effect of plasma protein binding, Int J Artif Organs January 1991; 14(1):43-50).

Bacterial endotoxins (lipopolysaccharides) are surfactants that are present in blood and other aqueous solutions in the form of aggregates, micelles and vesicles of various composition and structure (300 to 1000 kDa). These supramolecular structures may also contain blood plasma proteins and metal ions. The most conservative part of lipopolysaccharides is the "lipid A" fragment that contains phosphoryl groups and hydrophobic alkyl substituents. Sorbents with a hydrophobic matrix are known to bind lipopolysaccharides (see Chuichi Hirayama, Masayo Sakata, Chromatographic removal of endotoxin from protein solutions by polymer particles, Journal of Chromatography B, 781 (2002) 419-432 and F. B. Anspach, Endotoxin removal by affinity sorbents, J. Biochem. Biophys. Methods 49 (2001) 665-681).

Thus, a material that would bind lipopolysaccharides should have large pores with hydrophobic surface and easily accessible volume. We should note that lipopolysaccharide bacterial endotoxins are physiologically active (able to activate the immune system and increase the cytokine expression) even at concentrations as low as ~pg/mL, so that the problem of complete and efficient endotoxin removal is extremely important.

Thus, there is a need for new hemosorbents with high hemocompatibility that are able to remove both cytokines and bacterial endotoxins.

DETAILED DESCRIPTION OF THE INVENTION

The object of the invention is providing a new sorbent having high hemocompatibility and that is able to remove both cytokines and bacterial endotoxins from body fluids, such as blood, lymph, blood plasma, etc., as well as from aqueous solutions, including aqueous solutions of proteins and organic compounds that also contain inorganic salts, without influencing the composition and structure of other components of the said fluids.

Another object of this invention is providing easy, simple and effective methods of producing the above-mentioned sorbent.

Another object of this invention is providing easy and simple method of cleaning aqueous solutions of proteins and organic compounds that also contain inorganic salts, as well as cleaning body fluids, such as blood, lymph, blood plasma, etc., from contaminations, such as bacterial endotoxins (lipopolysaccharides) and cytokines.

These objects are solved by providing new methods of producing a polymer sorbent that is able to selectively bind both cytokines and bacterial endotoxins from body fluids, such as blood, lymph, blood plasma, etc., as well as from aqueous solutions, including aqueous solutions of proteins and organic compounds that also contain inorganic salts.

These objects are also solved by providing a new polymer sorbent, produced with the claimed methods and characterized by specific surface area of 610 to 1025 $m^2/g$, sorption capacity with respect to bacterial endotoxins of 170 to 5990 EU/mL, sorption capacity with respect to myoglobin of 3.4 to 17.2 mg/g, swelling by weight of 1.1 to 2.3 mL/g, hemolytic activity of 0% to 5.6% and pellet size of 1 to 1500 μm.

These objects are also solved by providing a new method of sorption removal of cytokines and bacterial endotoxins, which involves contacting the claimed sorbent and any one of the following fluids: body fluids, aqueous solutions of proteins and/or organic compounds that contain inorganic salts.

Thus, one aspect of the present invention relates to a method of producing a polymer sorbent that includes the following steps:

polymerizing or co-polymerizing of one or more monomers by mixing said one or more monomers with at least one polymeric amphiphilic compound and at least one porogen, and adding at least one polymerization initiator to a resulting mixture during constant mixing;

separating pellets obtained in result of the polymerizing from the dispersion media;

cross-linking the polymerized pellets with a cross-linking agent in a thermodynamically suitable solvent in the presence of a catalyst;

rinsing the resulting hypercrosslinked polymer pellets to remove the monomer residue, polymerization initiator residue, cross-linking agent residue and catalyst residue, and drying the resulting sorbent, characterized in that the separating the polymerized pellets from the dispersion media is carried out by adding cold water having a temperature ranged from 18° C. to 23° C. to the polymerization reaction mixture at a volume ratio reaction mixture:water ranged from 1:1 to 1:4 and then decanting. The resulting pellets are dried at 20° C. to 80° C. and cross-linked by the cross-linking agent.

Another aspect of the present invention relates to a method of producing a polymer sorbent that includes the following stages:

polymerizing or co-polymerizing of one or more monomers by mixing said one or more monomers with at least one polymeric amphiphilic compound and at least one porogen, and adding at least one polymerization initiator to a resulting mixture during constant mixing;

separating pellets obtained in result of the polymerizing from the dispersion media;

cross-linking the polymer pellets with a cross-linking agent in a thermodynamically suitable solvent in the presence of a catalyst;

rinsing the resulting hypercrosslinked polymer pellets to remove the monomer residue, polymerization initiator residue, cross-linking agent residue and catalyst residue, and drying the resulting sorbent, characterized in that the separating the polymerized pellets from the dispersion media is carried out by filtering, rinsing the separated pellets with hot water having a temperature ranged from 60° C. to 70° C. at a volume ratio pellets:water ranged from 1:1 to 1:4, then rinsing the pellets with cold water having a temperature ranged from 18° C. to 23° C. at a volume ratio pellets:water ranged from 1:1 to 1:4), then rinsing with acetone at volume ratio pellets:acetone ranged from 1:1 to 1:4 to remove the monomer residue, and rinsing with water until the water reaches a pH of 6 to 7, then the rinsed pellets are dried at 20° C. to 80° C. and cross-linked by the cross-linking agent.

In the claimed methods, one or more monomers can be selected from: styrene, α-methylstyrene, ethylstyrene, acrylonitrile, butyl methacrylate, butyl acrylate, vinylnaphthalene, vinyltoluene, vinylbenzyl alcohol, N-vinylpyrrolidone, vinylformamide, methyl methacrylate, methyl acrylate, dimethylaminoethyl methacrylate, dimethylaminoethyl acrylate, diethylaminoethyl methacrylate, acrylic acid, methacrylic acid, acrylamide, methacrylamide, glycidyl methacrylate, vinyl acetate, vinyl chloride, allylamine, allyl glycidyl ether, ethylene glycol dimethacrylate, triethylene glycol dimethacrylate, N,N-bismethacrylamide, divinylbenzene, trivinylbenzene, divinylnaphthalene, trivinylcyclohexane, divinyl sulfone, vinylacrylamide and mixtures thereof.

Preferred monomers are selected from: styrene; divinylbenzene; vinylpyrrolidone; diethylaminoethyl methacrylate; ethylene glycol dimethacrylate; allyl glycidyl ether; methyl methacrylate; glycidyl methacrylate; a mixture of styrene and divinylbenzene; a mixture of styrene and ethylene glycol dimethacrylate; a mixture of styrene, divinylbenzene and N-vinylpyrrolidone; a mixture of styrene, divinylbenzene and 1-vinylimidazole; a mixture of vinyltoluene and divinylbenzene; even more preferred are styrene, divinylbenzene or a mixture of styrene and divinylbenzene with styrene:divinylbenzene ratios of 99.9:0.01 vol. % to 0.01:99.9 vol. %, preferably from 90:10 vol. % to 10:90 vol. %, or from 80:20 vol. % to 20:80 vol. %, or from 70:30 vol. % to 30:70 vol. %, or from 40:60 vol. % to 60:40 vol. %, based on a total volume of the mixture of styrene and divinylbenzene, or a mixture of styrene and divinylbenzene with ratios within ranges that are intermediate ones for the above ranges, or a mixture of styrene and dinivylbenzene with ratios resulted by combining the ranges above and limits thereof.

In some implementations, the mixture of monomers, in addition to the above mixture of styrene and divinylbenzene, may contain up to 10 vol. %, preferably from 0.01 vol. % to 10 vol. %, or from 1 vol. % to 10 vol. %, or from 2 vol. % to 10 vol. %, or from 5 vol. % to 10 vol. %, or from 0.01 vol. % to 9 vol. %, or from 0.01 vol. % to 8 vol. %, or from 0.01 vol. % to 7 vol. %, or from 0.01 vol. % to 6 vol. %, or from 0.01 vol. % to 5 vol. %, based on a total volume of the monomer mixture, or any amount within the above ranges, intermediate ranges or ones resulted by combining said ranges and limits thereof, of at least one monomer selected from: α-methylstyrene, ethylstyrene, acrylonitrile, butyl methacrylate, butyl acrylate, vinylnaphthalene, vinyltoluene, vinylbenzyl alcohol, N-vinylpyrrolidone, 2-vinylpyridine, 4-vinylpyridine, vinylformamide, 1-vinylimidazole, methyl methacrylate, methyl acrylate, dimethylaminoethyl methacrylate, dimethylaminoethyl acrylate, diethylaminoethyl acrylate, diethylaminoethyl methacrylate, acrylic acid, methacrylic acid, acrylamide, methacrylamide, glycidyl methacrylate, vinyl acetate, vinyl chloride, allylamine, diallylamine, allyl glycidyl ether, ethylene glycol dimethacrylate, triethylene glycol dimethacrylate, N,N-bismethacrylamide, trivinylbenzene, divinylnaphthalene, trivinylcyclohexane, divinyl sulfone, vinylacrylamide and mixtures thereof.

If a mixture of styrene and ethylene glycol dimethacrylate is used, the ratio of styrene:ethylene glycol dimethacrylate should be the same as the ratio of styrene:divinylbenzene above.

If a mixture of vinyltoluene and divinylbenzene is used, the ratio of vinyltoluene:divinylbenzene should be the same as the ratio of styrene:divinylbenzene above.

The polymeric amphiphilic compound in the claimed methods above may be selected from: gelatin, albumin, carrageenan, glucomannan, guar gum, gum arabic, xanthan gum, carboxyethyl cellulose salts, hyaluronic acid salts, poly(maleic acid) salts, maleic acid/acrylic acid copolymer salts, maleic acid/methacrylic acid copolymer salts, poly(itaconic acid) salts, polyacrylamide, poly(methacrylamide), acrylamide/acrylic acid copolymer salts, methacrylamide/methacrylic acid copolymer salts, hydroxylethyl cellulose, hydroxypropyl cellulose, poly(hydroxyethyl acrylate), poly(hydroxyethyl methacrylate), poly(dimethylaminoethyl methacrylate), poly(dimethylaminoethyl acrylate), poly(diethylaminoethyl methacrylate), poly(N-vinylpyrrolidone), polyvinyl alcohol, polyethylene glycol, polypropylene glycol, polyethylene glycol/polypropylene glycol copolimer, polyacrylic acid salts, poly(methacrylic acid) salts and mixtures thereof. Preferred polymeric amphiphilic compounds are poly(vinylpyrrolidone), polyvinyl alcohol, polyethylene glycol. The most preferred compound is polyvinyl alcohol.

Any aliphatic alcohols with 3 to 18 carbon atoms and mixtures thereof may be used as porogens in the claimed method. Isoamyl alcohol or dodecanol are preferred as porogens. Dodecanol is the most preferred porogen.

Any compound that functions as polymerization initiators in the free-radical polymerization process may be used as the polymerization initiator in the claimed method. Examples of these compounds can be found, in particular, in a treatise "Macromolecules" by V. V. Kireev, published by "Vysshaya shkola", Moscow, 1992, pp. 120-128. In the present invention, benzoyl hydroxide or azobisisobutyronitrile are preferably used as polymerization initiators.

The cross-linking agent in the claimed methods may be selected from: chloromethyl methyl ether, thionyl chloride, p-xylylene dichloride, tris(chloromethyl)-trimethylbenzene, bis(chloromethyl) diphenyl butane, 1,4-bis(chloromethyl) biphenyl, dimethoxymethane, chloroform and any mixtures thereof. Preferable cross-linking agents are thionyl chloride, chloroform, chloromethyl methyl ether, dimethoxymethane or p-xylylene dichloride.

The thermodynamically suitable solvent in the claimed methods may be selected from: toluene, 1,2-dichloroethane, dichloromethane, chloroform, carbon tetrachloride, nitrobenzene, chlorobenzene and mixtures thereof. The preferred solvent is 1,2-dichloroethane.

The catalyst for the polymer pellet cross-linking may be selected from: aluminium chloride, iron(III) chloride, tin (IV) chloride, zinc chloride and titanium(IV) chloride.

Some embodiments of the present invention may include additional stages: preparing a solution 1 by dissolving the polymeric amphiphilic compound in water; preparing a solution 2 by adding the polymerization initiator to one or more monomers and adding the porogen to the resulting solution; mixing solution 1 and solution 2 to initiate the polymerization.

In some embodiments of the claimed methods polymerization is carried out at a temperature ranged 60° C. to 90° C. for 2 to 12 hours, preferably at 60° C. for 6 hours.

In some embodiments of the claimed methods the rotation speed during the polymerization is controlled, so that the resulting emulsion has drops and resulting polymer pellets sized from 1 μm to 1.5 mm, preferably from 50 μm to 1000 μm (1 mm), most preferably from 100 μm to 800 μm.

In some embodiments of the claimed methods the rotation speed during the polymerization can reach 500 rpm, preferably from 100 rpm to 500 rpm, most preferably from 120 rpm to 160 rpm.

Some embodiments of the claimed methods may include an additional stage of sifting the resulting sorbent pellets to obtain the desired size fraction. Preferably sifting is implemented using standard sieves with 1.0 mm, 0.8 mm, 0.5 mm and/or 0.3 mm mesh size. Most preferably sifting is implemented using sets of standard sieves allowing to obtain a size fraction with sizes from 300 μm to 1.0 mm, or from 300 μm to 800 μm, or from 300 μm to 500 μm.

According to the present invention, the polymeric amphiphilic compound may be used in an amount ranged from 0.25 wt. % to 5.00 wt. % based on a total weight of the monomer or monomer mixture to be used, preferably from 1.00 wt. % to 5.00 wt. %, or from 1.00 wt. % to 4.00 wt. %, or from 1.00 wt. % to 3.00 wt. %, or from 1.00 wt. % to 2.00 wt. % of total monomer or monomer mixture weight, most preferably from 1.00 wt. % to 1.50 wt. % of the total monomer or monomer mixture weight.

In some embodiments the resulting pellets of hypercross-linked polymer are rinsed with acetone and water to remove monomer residue, polymerization initiator residue, cross-linking agent residue and catalyst residue as long as the rinsing water contains chlorine ions.

According to the present invention, the porogen may be used in an amount ranged from 5 vol. % to 200 vol. % base on a total volume of a monomer to be used or a monomer starting mixture to be used, preferably from 30 vol. % to 200 vol. %, or from 50 vol. % to 200 vol. %, or from 50 vol. % to 100 vol. %, or from 75 vol. % to 100 vol. %, or in any amount within the ranges above, the intermediate ranges or ones resulted from combining the above ranges and limits thereof.

According to the present invention, the cross-linking agent may be used in an amount ranged from 10 mol. % to 500 mol. % based on a total amount of the polymer obtained in course of polymerization or copolymerization, preferably from 25 mol. % to 500 mol. %, or from 50 mol. % to 500 mol. %, or from 75 mol. % to 500 mol. %, or from 100 mol. % to 500 mol. %, or from 150 mol. % to 500 mol. %, or from 200 mol. % to 500 mol. %, or from 10 mol. % to 450 mol. %, or from 25 mol. % to 450 mol. %, or from 50 mol. % to 400 mol. %, or from 100 mol. % to 350 mol. %, or from 150 mol. % to 300 mol. %, or from 150 mol. % to 250 mol. %, or any amount within the ranges above, the intermediate ranges or ones resulted from combining the above ranges and limits thereof.

According to the present invention, the thermodynamically suitable solvent may be used in an amount ranged from 200 vol. % to 1000 vol. % based on a total volume of the polymer obtained in course of the polymerization or copolymerization, preferably from 250 vol. % to 1000 vol. %, or from 300 vol. % to 1000 vol. %, or from 350 vol. % to 1000 vol. %, or from 450 vol. % to 1000 vol. %, or from 500 vol. % to 1000 vol. %, or from 550 vol. % to 1000 vol. %, or from 600 vol. % to 1000 vol. %, or from 700 vol. % to 1000 vol. %, or from 200 vol. % to 900 vol. %, or from 200 vol. % to 800 vol. %, or from 200 vol. % to 700 vol. %, or from 200 vol. % to 600 vol. %, or from 200 vol. % to 500 vol. %, or any amount within the ranges above, the intermediate ranges or ones resulted from combining the above ranges and limits thereof.

According to the present invention, the cross-linking catalyst bay be used in an amount ranged from 0.1 mol. % to 5.0 mol. % based on an amount of the polymer obtained in course of the polymerization or copolymerization, preferably from 1.0 mol. % to 5.0 mol. %, or from 1.5 mol. % to 5.0 mol. %, or from 2.0 mol. % to 5.0 mol. %, or from 2.5 mol. % to 5.0 mol. %, or from 3.0 mol. % to 5.0 mol. %, or from 3.5 mol. % to 5.0 mol. %, or from 4.0 mol. % to 5.0 mol. %, or from 0.1 mol. % to 4.5 mol. %, or from 1.0 mol. % to 4.5 mol. %, or from 1.0 mol. % to 4.0 mol. %, or from 1.5 mol. % to 3.5 mol. %, or from 2.0 mol. % to 3.0 mol. %, or in any amount within the ranges above, the intermediate ranges or ones resulted from combining the above ranges and limits thereof.

Some preferable embodiments of the claimed methods may include an additional step, wherein the hypercross-linked polymer-based sorbent is modified by at least one ligand selected from: ammonia, methylamine, butylamine, dimethylamine, diethylamine, ethylenediamine, 2-ethanolamine, imidazole, 1-methylimidazole, 2-methylimidazole, histamine, histidine, lysine, arginine, ε-polylysine, diethylenetriamine, diethylenetetramine, triethylenetetramine, tetraethylenepentamine, polyethylene polyamine, polyethylenimine, chitosan, polymyxin B, colistin, optionally modified by at least one N-acylating agent or N-alkylating agent, selected from $C_1$-$C_{18}$ aliphatic compounds, including, but not limited to the following list: methyl iodide, dimethyl sulfate, ethyl iodide, bromoethane, 1-bromopropane, 1-chloropropane, 2-bromopropane, 2-chloropropane, 1-bromobutane, 1-chlorobutane, 1-bromopentane, 1-chloropentane, 1-bromo-2-methylpropane, 1-chloro-2-methylpropane, 1-bromo-3-methylbutane, 1-chloro-3-methylbutane, 1-bromohexane, 1-chlorohexane, 1-bromoheptane, 1-chloroheptane, 1-bromooctane, 1-chlorooctane, 1-bromononane, 1-chlorononane, 1-bromodecane, 1-chlorodecane, 1-bromoundecane, 1-chloroundecane, 1-bromododecane, 1-chlorododecane, 1-bromotridecane, 1-chlorotridecane, 1-bromotetradecane, 1-chlorotetradecane, 1-bromopentadecane, 1-chloropentadecane, 1-bromohexadecane, 1-chlorohexadecane, 1-bromoheptadecane, 1-chloroheptadecane, 1-bromooctadecane, 1-chlorooctadecane, acetyl chloride, acetic anhydride, propionyl chloride, propionic anhydride, butyryl chloride, valeroyl chloride, hexanoyl chloride, heptanoyl chloride, octanoyl chloride, nonanoyl chloride, decanoyl chloride, undecanoyl chloride, dodecanoyl chloride, tridecanoyl chloride, tetradecanoyl chloride, pentadecanoyl chloride, hexadecanoyl chloride, heptadecanoyl chloride, octadecanoyl chloride.

Methods to modify the hypercrosslinked polymer-based sorbent by the above ligands according to the present invention are known, for instance, from:

1. Cationic polystyrene spheres for removal of anionic contaminants in white water of papermaking//He Xiao, Beihai He, Liying Qian, Junrong Li. Journal of Applied Polymer Science, 132 (5) Feb. 5, 2015

2. Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10 Oct. 1977 Pages 2589-2596

However, the present invention is not limited to these modification methods. In essence, the sorbent claimed by the present invention can be modified by any polymer modification method known from the prior art and suitable for the polymers comprising or consisting of monomers composing the sorbent claimed by the present invention. Examples of such methods are given, for instance, in: Synthesis of Functional Polymers by Post-Polymerization Modification//Marc A. Gauthier Dr., Matthew I. Gibson Dr., Harm-Anton Klok Prof. Dr. Angewandte Chemie, Volume 48, Issue 1, Dec. 22, 2008 Pages 48-58; Standing on the shoulders of Hermann Staudinger: Post-polymerization modification from past to present//Kemal Arda Giinay, Patrick Theato, Harm-Anton Klok. Journal of Polymer Science part A, Volume 51, January 2013, Pages 1-28; Amidomethylation of Vinyl Aromatic Polymers with N-Methylol-2-chloroacetamide//Kazuo Teramoto, Yoshiaki Nakamoto. Polymer Journal, Vol. 34, No. 5, pp 363-369 (2002).

Another aspect of the present invention relates to a polymer sorbent, produced with the claimed methods and characterized by specific surface area of 610 to 1025 $m^2/g$, sorption capacity with respect to bacterial endotoxins of 170 to 5990 EU/mL, sorption capacity with respect to myoglobin of 3.4 to 17.2 mg/g, swelling by weight of 1.1 to 2.3 mL/g, hemolytic activity of 0% to 5.6%.

In one of the embodiments, the claimed sorbent is characterized by the pellets size from 1 μm to 1500 μm.

In some of the embodiments, the claimed sorbent may be characterized by the pellets size from 50 μm to 1000 μm (1 mm), preferably from 100 μm to 800 μm.

In most preferable embodiments, the claimed sorbent consists of pellets with sizes ranging from 300 μm to 1.0 mm, or from 300 μm to 800 μm, or from 300 μm to 500 μm.

Another aspect of the present invention relates to the method of sorption removal of cytokines and bacterial endotoxins from a fluid selected from: body fluids, aqueous solutions of proteins and/or organic compounds that contain inorganic salts, which involves contacting said fluid with the claimed sorbent.

In the preferred embodiment of the method of sorption removal the fluid to be treated is a body fluid.

In another preferred embodiment the body fluid to be treated may be blood, lymph, blood plasma, cerebrospinal fluid, peritoneal fluid.

The claimed method is suitable to treat aqueous solution of proteins, aqueous solutions of polysaccharides, aqueous solutions of synthetic organic compounds that make up medicinal drugs and their precursors, infusion solutions, culture fluids.

In the preferred embodiment of the sorption removal method the fluid to be treated is kept in contact with the claimed sorbent for the period from 1 hour to 12 hours, preferably from 2 hours to 4 hours.

In the preferred embodiment of the sorption removal method the body fluid to be treated is collected from the patient's body, passed through a cartridge filled with the claimed sorbent in an external circuit, and returned to the body after having been in contact with the claimed sorbent.

In some preferred embodiments of the claimed sorption removal method, the fluid flow velocity through the cartridge can be from 50 mL/min to 250 mL/min. The fluid pressure can reach 100 mm Hg to 400 mm Hg. This aspect and other details of the claimed sorption removal method are identical to the figures of merit for similar sorption removal methods in prior art (see the manual for the TORAYMYXIN PMX-20R extracorporal hemoperfusion cartridge, 2006).

Without wishing to be bound by any particular theory, the inventors suppose that the claimed sorbent production method is different from methods in prior art in that it allows to cross-link the polymer in the presence of one or more polymeric amphiphilic compounds selected from: gelatin, albumin, carrageenan, glucomannan, guar gum, gum arabic, xanthan gum, carboxyethyl cellulose salts, hyaluronic acid salts, poly(maleic acid) salts, maleic acid/acrylic acid copolymer salts, maleic acid/methacrylic acid copolymer salts, poly(itaconic acid) salts, polyacrylamide, poly(methacrylamide), acrylamide/acrylic acid copolymer salts, methacrylamide/methacrylic acid copolymer salts, hydroxyethyl cellulose, hydroxypropyl cellulose, poly(hydroxyethyl acrylate), poly(hydroxyethyl methacrylate), poly(dimethylaminoethyl methacrylate), poly(dimethylaminoethyl acrylate), poly(diethylaminoethyl methacrylate), poly(N-vinylpyrrolidone), polyvinyl alcohol, polyethylene glycol, polypropylene glycol, polyethylene glycol/polypropylene glycol copolimer, polyacrylic acid salts, poly(methacrylic acid) salts and mixtures thereof that were present during polymer production. The authors of the present invention suppose that the difference come from the distinctive method of sorbent production: in the claimed method, the resulting pellets of the polymer before cross-linking are separated from the reaction mixture (that contains, in particular, the above mentioned polymeric amphiphilic compounds) by adding cold water (18° C. to 23° C., with volume ratio 1:2 reaction mixture:water) to the polymerization reaction mixture and decanting; the resulting pellets are dried at 20° C. to 80° C. and cross-linked by the cross-linking agent; alternatively, the polymer pellets are separated by filtering and rinsing the resulting pellets with hot water (60° C. to 70° C., with volume ratio 1:1 to 1:4 pellets:water), rinsing the pellets with cold water (18° C. to 23° C., with volume ratio 1:1 to 1:4 pellets:water), rinsing with acetone with volume ratio 1:1 to 1:4 pellets:acetone to remove the monomer residue, and rinsing with water until the water reaches a pH of 6 to 7. The rinsed pellets are dried at 20° C. to 80° C. and cross-linked with a cross-linking agent. Without wishing to be bound by any particular theory, the inventors suppose that the above mentioned details of the production method allow to obtain the pellets with a distinctive hypercrosslinked polymer structure. In particular, the presence of the polymeric amphiphilic compounds (surfactants) during the polymer cross-linking apparently blocks the pellet surface and large pores (20 nm and larger) from being accessible to small molecules of cross-linking agents. The molecules of these polymeric surfactants are large enough to preferentially adsorb on the surfaces of large (20 nm and larger) pores and pellet surfaces, without adsorbing on the smaller pores and without blocking smaller pores. At the same time, these surfactants can be removed during subsequent rinsing of the sorbent pellets. Thus, the claimed method is different from the known prior methods of hemocompatible sorbent production in that the surfactants are not used to increase the biocompatibility of the hypercrosslinked polymer-based sorbent and do not comprise the final product. Instead, the surfactants are used as auxiliary process material, do not form covalent bonds with the substrate material, do not form hydrophobic-hydrophilic bonds with the substrate material, do not contact the body fluids and are not involved in the sorption processes. Without wishing to be bound by any particular theory, the inventors suppose that this approach allows to produce a hypercrosslinked polymer-based sorbent with a distinctive pore morphology that is different from the pore morphology in similar materials. The authors of the present invention suppose that due to the above-mentioned details in the claimed sorbent the surface areas of the large (20 nm and larger) pores, that adsorb lipopolysaccharides, are characterized by a lower degree of cross-linking and a higher hydrophobicity due to a slower transport of cross-linking agents. At the same time, the material obtained by the claimed method is as hemocompatible as hypercrosslinked polystyrene obtained with prior art methods. It is shown that this approach allows for more efficient lipopolysacchharide sorption without compromising hemocompatibility and cytokine sorption due to sorption in smaller pores.

Thus, the inventors suppose that the combination of the above factors allow to obtain a sorbent with high hemocompatibility and high selective sorption of both cytokines and bacterial endotoxins.

As described above, the technical result of the present invention is an easy and effective method of producing a polymer sorbent with high hemocompatibility that can selectively remove both cytokines and bacterial endotoxins from various fluids; another technical result is a new polymer sorbent obtained with the claimed method and characterized by the above qualities. The claimed sorbent can form both ionic and hydrophobic bonds with bacterial endotoxins, which allows for a synergistic effect and a high sorption capacity of the material under a range of external conditions (solution concentration, pH, ionic strength). Another technical result of the present invention is a new method of sorption removal of cytokines and bacterial endotoxins from fluids, which employs the claimed polymer sorbent. The characteristics of the claimed sorbent allow for an easier and more reliable fluid treatment, eliminating the separate cytokine removal and bacterial endotoxin removal processes. This decreases the fluid loss, lowers the process requirements for the equipment that implements the claimed method, and lowers the risk of contaminating the fluid during the treatment.

EXAMPLES

The examples that follow are purely illustrative. They are given to demonstrate that the claimed invention is a feasible way of obtaining the claimed technical results. Under no circumstances these examples should limit the scope and the essence of the claimed inventions.

Example 1

1 L of water is placed into a 2 L three-necked flask with an anchor agitator, a reflux condenser and a thermometer. 3.3 g of polyethylene glycol (Mw 4000) is dissolved in water at 60° C. while stirring to be used as the polymeric amphiphilic compound. The resulting clear solution (solution 1) is cooled to room temperature. 170 mL of styrene to be used as the initial monomer mixture is placed in a separate vessel. 3.3 g of benzoyl peroxide, to be used as the polymerization initiator, is dissolved in styrene. 110 mL of isoamyl alcohol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 80° C.

Example 2

1 L of water is placed into a 2 L three-necked flask with an anchor agitator, a reflux condenser and a thermometer. 3.1 g of polyvinyl alcohol (Mw 28000) is dissolved in water at 60° C. while stirring to be used as the polymeric amphiphilic compound. The resulting clear solution (solution 1) is cooled to room temperature. 170 mL of divinylbenzene to be used as the initial monomer mixture is placed in a separate vessel. 3.3 g of azobisisobutyronitrile, to be used as the polymerization initiator, is dissolved in divinylbenzene. 120 mL of dodecanol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 80° C.

Example 3

1 L of water is placed into a 2 L three-necked flask with an anchor agitator, a reflux condenser and a thermometer. 3.5 g of polyvinylpirrolidone (Mw 40000) is dissolved in water at 60° C. while stirring to be used as the polymeric amphiphilic compound. The resulting clear solution (solution 1) is cooled to room temperature. 155 mL of styrene and 15 mL of divinylbenzene to be used as the initial monomer mixture are placed in a separate vessel. 3.3 g of benzoyl peroxide, to be used as the polymerization initiator, is dissolved in the mixture. 170 mL of isoamyl alcohol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 80° C.

Example 4

1 L of water is placed into a 2 L three-necked flask with an anchor agitator, a reflux condenser and a thermometer. 3.3 g of polyvinyl alcohol (Mw 28000) is dissolved in water at 60° C. while stirring to be used as the polymeric amphiphilic compound. The resulting clear solution (solution 1) is cooled to room temperature. 140 mL of styrene, 15 mL of divinylbenzene, and 15 mL of N-vinylpyrrolidone to be used as the initial monomer mixture are placed in a separate vessel. 3.3 g of azobisisobutyronitrile, to be used as the polymerization initiator, is dissolved in the mixture. 90 mL of dodecanol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 20° C.

Example 5

1 L of water is placed into a 2 L three-necked flask with an anchor agitator, a reflux condenser and a thermometer. 3.3 g of polyethylene glycol (Mw 4000) is dissolved in water at 60° C. while stirring to be used as the polymeric amphiphilic compound. The resulting clear solution (solution 1) is cooled to room temperature. 140 mL of styrene, 15 mL of divinylbenzene, and 15 mL of 1-vinylimidazole to be used as the initial monomer mixture are placed in a separate vessel. 3.3 g of benzoyl peroxide, to be used as the polymerization initiator, is dissolved in the mixture. 150 mL of isoamyl alcohol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 50° C.

Example 6

1 L of water is placed into a 2 L three-necked flask with an anchor agitator, a reflux condenser and a thermometer. 3.3 g of polyvinylpirrolidone (Mw 40000) is dissolved in water at 60° C. while stirring to be used as the polymeric amphiphilic compound. The resulting clear solution (solution 1) is cooled to room temperature. 155 mL of styrene and 15 mL of ethylene glycol dimethacrylate to be used as the initial monomer mixture are placed in a separate vessel. 3.3 g of benzoyl peroxide, to be used as the polymerization initiator, is dissolved in the mixture. 160 mL of dodecanol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 70° C.

Example 7

1 L of water is placed into a 2 L three-necked flask with an anchor agitator, a reflux condenser and a thermometer. 3.3 g of polyvinyl alcohol (Mw 28000) is dissolved in water at 60° C. while stirring to be used as the polymeric amphiphilic compound. The resulting clear solution (solution 1) is cooled to room temperature. 140 mL of styrene, 15 mL of divinylbenzene, and 15 mL of allyl glycidyl ether to be used as the initial monomer mixture are placed in a separate vessel. 3.3 g of benzoyl peroxide, to be used as the polymerization initiator, is dissolved in the mixture. 85 mL of isoamyl alcohol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 60° C.

Example 8

1 L of water is placed into a 2 L three-necked flask with an anchor agitator, a reflux condenser and a thermometer. 3.5 g of polyethylene glycol (Mw 4000) is dissolved in water at 60° C. while stirring to be used as the polymeric amphiphilic compound. The resulting clear solution (solution 1) is cooled to room temperature. 155 mL of vinyltoluene and 15 mL of divinylbenzene to be used as the initial monomer mixture are placed in a separate vessel. 3.3 g of azobisisobutyronitrile, to be used as the polymerization initiator, is dissolved in the mixture. 140 mL of dodecanol is added to the resulting solution (solution 2) to be used as the porogen. Solution 2 is added to solution 1 while stirring at 130 rpm to 135 rpm. Heating is turned on. The size of the forming droplets is controlled visually or with a microscope. If needed, the agitation speed can be adjusted to keep the size of the droplets equal to the intended pellet size. Polymerization is carried out at 80° C. and constant agitation for 6 hours. The resulting pellets are rinsed with hot water (60° C. to 70° C., 1:1 to 1:3 pellets:water volume ratio), then with cold water (18° C. to 23° C., 1:1 to 1:3 pellets:water volume ratio), then with acetone (1:1 to 1:3 pellets:acetone volume ratio) to remove the monomer residue. The pellets are then rinsed with water until the water reaches a pH of 6 or 7. The rinsed pellets are then dried in a drying cabinet at 20° C.

Example 9

180 g of chloromethyl methyl ether, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 1 is added to the resulting solution while slowly agitating. The reaction mixture is cooled with ice to +5° C. 100 g of tin(IV) chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 10

180 g of chloromethyl methyl ether, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 2 is added to the resulting solution while slowly agitating. The reaction mixture is cooled with ice to +5° C. 45.3 g of zinc chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 11

180 g of chloromethyl methyl ether, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 3 is added to the resulting solution while slowly agitating. The reaction mixture is cooled with ice to +5° C. 89.2 g of iron(III) chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 12

453 g of p-xylylene dichloride, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 4 is added to the resulting solution while slowly agitating. The reaction mixture is cooled with ice to +5° C. 47.3 g of aluminium chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 13

453 g of p-xylylene dichloride, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 5 is added to the resulting solution while slowly agitating. The reaction mixture is cooled with ice to +5° C. 45.3 g of zinc chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 14

172 g of dimethoxymethane, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 6 is added to the resulting solution while slowly agitating. The reaction mixture is cooled with ice to +5° C. 89.2 g of iron(III) chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 15

172 g of dimethoxymethane, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 7 is added to the resulting solution while slowly agitating. The reaction mixture is cooled with ice to +5° C. 100 g of tin(IV) chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 16

180 g of chloromethyl methyl ether, to be used as the cross-linking agent, and 540 mL of dry 1,2-dichloroethane, to be used as the solvent, are mixed in a three-neck flask with an anchor agitator, a thermometer and a reflux condenser with a calcium chloride tube connected to a gaseous hydrogen chloride absorption system. 105 g of dry macroporous copolymer according to example 8 is added to the resulting solution while slowly agitating. The reaction mixture is cooled with ice to +5° C. 45.3 g of zinc chloride, to be used as the catalyst, is slowly added to the reaction mixture while agitating. The mixture is heated to 80° C. The reaction is carried out at 80° C. for 8 hours to 10 hours. The pellets are cooled to room temperature, rinsed with acetone and water until no chlorine ions remain in water.

Example 17

10 mL of dry polymer according to example 3 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of imidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 18

10 mL of dry polymer according to example 9 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 19

10 mL of dry polymer according to example 10 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 20

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 21

10 mL of dry polymer according to example 12 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 22

10 mL of dry polymer according to example 13 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596).

20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 23

10 mL of dry polymer according to example 14 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 24

10 mL of dry polymer according to example 15 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 25

10 mL of dry polymer according to example 16 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 2-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 26

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 0.7 mL of saturated aqueous ammonia is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 27

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 3.6 mL of saturated methylamine aqueous solution is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 28

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 1.7 mL of octadecylamine is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 29

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 3.8 mL of saturated dimethylamine aqueous solution is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 30

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 3.8 mL of saturated diethylamine aqueous solution is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 31

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 1.85 mL of ethylenediamine is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 32

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 1.95 mL of ethanolamine is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Example 33

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2 g of 1-methylimidazole is added. The reaction is carried out for 48 hours while boiling. The sorbent is transfered onto a fritted glass filter with class 3 porosity (ISO 4793, 16 μm to 40 μm), filtered, rinsed with ethanol (8.15 mL), and air dried.

Example 34

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2.2 g of histamine is added. The reaction is carried out for 48 hours while boiling. The sorbent is transfered onto a fritted glass filter with class 3 porosity (ISO 4793, 16 µm to 40 µm), filtered, rinsed with ethanol (8.15 mL), and air dried.

Example 35

10 mL of dry polymer according to example 10 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2.3 g of L-histidine is added. The reaction is carried out for 48 hours while boiling. The sorbent is transfered onto a fritted glass filter with class 3 porosity (ISO 4793, 16 µm to 40 µm), filtered, rinsed with ethanol (8.15 mL), and air dried.

Example 36

10 mL of dry polymer according to example 10 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 1.8 g of L-lysine is added. The reaction is carried out for 48 hours while boiling. The sorbent is transfered onto a fritted glass filter with class 3 porosity (ISO 4793, 16 m to 40 µm), filtered, rinsed with ethanol (8.15 mL), and air dried.

Example 37

10 mL of dry polymer according to example 10 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 1.8 g of poly(ε-lysine) is added. The reaction is carried out for 48 hours while boiling. The sorbent is transfered onto a fritted glass filter with class 3 porosity (ISO 4793, 16 µm to 40 µm), filtered, rinsed with ethanol (8.15 mL), and air dried.

Example 38

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2.6 mL of diethylenetriamine is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 39

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 3.1 mL of triethylenetetramine is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 40

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 3.7 mL of Ni-undecyl carbonyl tetraethylenepentamine is added. The reaction is carried out for 6 hours at room temperature. The sorbent is transfered onto a fritted

Example 41

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2.6 mL of polyethylene polyamine is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 42

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 2.3 mL of polyethylenimine is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 43

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 0.5 g of chitosan is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 44

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 0.3 g of polymyxine B is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 45

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 0.3 g of ε-polylysine is added. The reaction is carried out for 6 hours at room temperature. The sorbent is transfered onto a fritted glass filter with class 3 porosity (ISO 4793, 16 µm to 40 µm), filtered, rinsed with ethanol (8.15 mL), and air dried.

Example 46

10 mL of dry polymer according to example 11 is placed in a 100 mL round-bottom flask. The polymer should contain reactive functional groups (e. g., chloromethyl groups, bromomethyl groups, iodomethyl groups, sulfochloride groups, sulfonyl chloride groups, phosphoryl chloride groups, sulfo groups, carboxy groups, formyl groups, carbonyl chloride groups, etc., that are optionally introduced according to known methods, for example, according to Synthesis of copper(II) complexes of asymmetric resins prepared by attachment of α-amino acids to crosslinked polystyrene//M. A. Petit, J. Jozefonvicz. Journal of Applied Polymer Science, Volume 21, Issue 10, October 1977, pages 2589-2596). 20 mL of ethanol is added to be used as the solvent. The reaction mixture is left for 15 min of wetting at room temperature. 0.3 g of colistin is added. The reaction is carried out for 6 hours at room temperature. The sorbent is transfered onto a fritted glass filter with class 3 porosity (ISO 4793, 16 μm to 40 μm), filtered, rinsed with ethanol (8.15 mL), and air dried.

Examples 47 to 54

The production of polymer pellets in examples 47 to 54 follows the procedure in examples 1 to 8 correspondingly, with the following exception: after the polymerization is complete, the resulting polymer pellets are separated by adding water (18° C. to 23° C., 1:2 reaction mixture:water volume ratio) to the reaction mixture, decanting and drying, as described in examples 1 to 9.

Examples 55 to 62

The polymer pellets according to examples 47-54 are cross-linked according to procedures in examples 9-16, correspondingly.

Examples 63 to 92

The sorbents according to examples 47-54 are modified according to procedures in examples 17-46, correspondingly.

Sorbent Properties

The specific surface area of the sorbents was determined with the following procedure. A sorbent sample was degassed under vacuum at 50° C. for 24 hours.

The specific surface area was determined by the nitrogen adsorption method at −195.75° C. BET theory was used for the calculations. The obtained data are shown in table 1.

The sorption capacity of the sorbents with respect to bacterial endotoxins was determined with the following procedure. 7.5 mL of whole blood was contaminated with a standard bacterial endotoxin (*E. Coli* O13:H10) sample to obtain 400 EU/mL endotoxin concentration. The contaminated blood was added to a 0.5 mL sample of wet hemosorbent. The resulting suspension was stirred for 1 hour on a vortex mixer at 500 rpm.

The blood was centrifuged for 10 min at 3500 rpm (1000 g) and pre-treated. The bacterial endotoxin content was determined by the spectrophotometry of the endpoint chromogenic LAL assays, using the PYROCHROME reagents, according to OFS (Russian pharmacopoeia standards) "1.2.4.0006.15 Bacterial endotoxins".

Plasma from the whole blood with no bacterial endotoxins was used as a negative control sample.

Plasma from the whole blood contaminated with 400 EU/mL of bacterial endotoxin was used as a positive control sample. The sorbent capacity was determined as:

$$\text{Capacity, } EU/ml = \frac{(C_0 - C) * V_b}{V_s},$$

where:
$C_0$ is the initial endotoxin concentration in blood (400 EU/mL);
C is the endotoxin concentration after sorption;
$V_b$ is the circulating blood volume (7.5 mL);
$V_s$ is the sorbent volume (0.5 mL).

The sorption capacity of the sorbents with respect to myoglobin was determined with the following procedure. Sorbents are weighed, rinsed with ethanol, then rinsed with an excess of deionized water until the solvent is completely substituted, as controlled by spectrophotometry. The water residue is removed on a fritted glass filter in a low vacuum. A sorbent sample (250 mg to 275 mg) is placed in a myoglobin solution (0.2 mg/mL) in a phosphate buffer solution (pH 7.4, 0.05 M). The mixture is incubated at room temperature for 4 hours while vigorously mixing on a vortex mixer. Spectrophotometry measurements are carried out at 410 nm. The sorption activity is reported in mg/mL. The obtained data are shown in table 1.

The swelling by weight of the sorbents was determined with the following procedure. An excess of toluene is added to a small sample (0.4 g to 0.5 g) of the polymer. Polymer is left to swell for 12 hours. The polymer is then transferred to a porous-bottomed tube. The excess solvent is filtered out. The tube is tightly closed and centrifuged at 4000 rpm for 15 minutes to remove the inter-pellet liquid residue. The swelled sample is rapidly transferred to a pre-weighed weighing bottle. The weighing bottle is closed and weighed. The polymer is then dried at 100° C. in a drying cabinet until its weight settles. The swelling by weight is calculated as the solvent volume (in mL) absorbed by 1 g of dry polymer. The following formula was used for the calculations:

$$X = \frac{(m_1 - m_0)}{m_0 \cdot d},$$

where:
X is swelling by weight (mL/g);
$m_1$ is the mass of the swelled polymer (g);
$m_0$ is the mass of the dry polymer (g);
d is the solvent density (g/mL).

The obtained data are shown in table 1.

The hemolytic effect of the sorbents was determined with the following procedure.

A sample of whole blood was added to a small sample (0.4 g to 0.5 g) of the polymer. The mixture was incubated at room temperature for 60 minutes. The mixture was then centrifuged at 3500 rpm (1000 g) for 10 minutes. The free hemoglobin absorption at the 411 nm wavelength was determined. The hemolysis level was calculated as:

$$\text{hemolysis, } \% = \frac{A - A_0}{A_1 - A_0} \times 100 \%$$

where A is the sample absorption at 411 nm;
$A_0$ is the negative control sample absorption at 411 nm;
$A_1$ is the positive control sample absorption at 411 nm.

The plasma from the whole blood was incubated at room temperature for 60 minutes and used as a negative control sample.

0.9 mL of whole blood was treated with 100 μL of 10% Triton X-100 solution, incubated at room temperature for 60 minutes and centrifuged. The hemoglobin content was determined with a standard procedure.

TABLE 1

| | specific surface area (m²/g) | Capacity w.r.t LPS (EU/mL) | Capacity w.r.t myoglobin (mg/g) | swelling in water (mg/mL) | hemolysis (%) |
|---|---|---|---|---|---|
| example 1 | 45 | 460 | 4.7 | 0.2 | 5.7 |
| example 2 | 34 | 340 | 4.5 | 0.3 | 4.9 |
| example 3 | 53 | 270 | 12.4 | 0.3 | 7.3 |

TABLE 1-continued

| | specific surface area (m²/g) | Capacity w.r.t LPS (EU/mL) | Capacity w.r.t myoglobin (mg/g) | swelling in water (mg/mL) | hemolysis (%) |
|---|---|---|---|---|---|
| example 4 | 48 | 380 | 10.1 | 0.4 | 6.2 |
| example 5 | 39 | 400 | 11.9 | 0.4 | 5.8 |
| example 6 | 62 | 520 | 13.4 | 0.3 | 5.5 |
| example 7 | 58 | 430 | 7.4 | 0.5 | 7.1 |
| example 8 | 46 | 500 | 3.5 | 0.3 | 5.2 |
| example 9 | 786 | 1700 | 5.8 | 1.2 | 0.9 |
| example 10 | 847 | 2100 | 9.9 | 1.5 | 0.9 |
| example 11 | 1025 | 2200 | 17.2 | 1.5 | 0.5 |
| example 12 | 913 | 220 | 7.3 | 1.9 | 5.6 |
| example 13 | 880 | 160 | 8.2 | 1.3 | 5.7 |
| example 14 | 994 | 2060 | 15.7 | 1.7 | 0.6 |
| example 15 | 610 | 1850 | 9.4 | 1.6 | 0.8 |
| example 16 | 824 | 1770 | 5.5 | 1.1 | 0.9 |
| example 17 | 44 | 980 | 11.5 | 2.0 | 4.7 |
| example 18 | 762 | 2800 | 6.5 | 1.9 | 1.3 |
| example 19 | 830 | 3100 | 9.7 | 2.1 | 1.1 |
| example 20 | 1019 | 340 | 15.4 | 1.5 | 5.3 |
| example 21 | 874 | 420 | 12.0 | 1.4 | 5.5 |
| example 22 | 755 | 2890 | 11.4 | 1.7 | 0.9 |
| example 23 | 923 | 3070 | 12.8 | 1.9 | 0.8 |
| example 24 | 787 | 2360 | 7.9 | 2.0 | 1.1 |
| example 25 | 802 | 2220 | 4.7 | 1.4 | 1.2 |
| example 26 | 1021 | 2490 | 15.1 | 1.5 | 0.7 |
| example 27 | 1010 | 2590 | 15.8 | 1.5 | 0.9 |
| example 28 | 996 | 2560 | 15.8 | 1.7 | 0.6 |
| example 29 | 998 | 2330 | 15.0 | 2.0 | 0.9 |
| example 30 | 970 | 2470 | 15.4 | 2.1 | 1.1 |
| example 31 | 989 | 2800 | 14.7 | 1.5 | 1.2 |
| example 32 | 980 | 2650 | 14.9 | 1.3 | 0 |
| example 33 | 992 | 3300 | 15.5 | 1.8 | 0.9 |
| example 34 | 1009 | 4830 | 16.2 | 1.9 | 0.5 |
| example 35 | 1012 | 4980 | 16.0 | 1.9 | 0.4 |
| example 36 | 996 | 4650 | 14.7 | 1.9 | 0.7 |
| example 37 | 990 | 4240 | 14.9 | 1.8 | 0.5 |
| example 38 | 834 | 5670 | 12.3 | 2.0 | 1.3 |
| example 39 | 976 | 3240 | 15.3 | 2.1 | 1.1 |
| example 40 | 984 | 3410 | 15.2 | 2.1 | 1.2 |
| example 41 | 985 | 3660 | 15.8 | 2.2 | 1.4 |
| example 42 | 787 | 5530 | 10.1 | 2.3 | 1.5 |
| example 43 | 725 | 3020 | 14.0 | 2.1 | 1.3 |
| example 44 | 840 | 5780 | 6.7 | 1.9 | 0.4 |
| example 45 | 957 | 5990 | 15.1 | 1.5 | 1.1 |
| example 46 | 960 | 5980 | 15.3 | 1.5 | 1.1 |
| example 47 | 46 | 460 | 4.6 | 0.2 | 5.5 |
| example 48 | 33 | 340 | 4.5 | 0.3 | 4.9 |
| example 49 | 57 | 270 | 12.4 | 0.3 | 7.3 |
| example 50 | 47 | 380 | 10.2 | 0.4 | 6.2 |
| example 51 | 38 | 400 | 11.9 | 0.4 | 5.8 |
| example 52 | 60 | 520 | 13.4 | 0.3 | 5.6 |
| example 53 | 58 | 430 | 7.4 | 0.5 | 7.1 |
| example 54 | 46 | 500 | 3.4 | 0.3 | 5.3 |
| example 55 | 783 | 1710 | 5.7 | 1.2 | 0.9 |
| example 56 | 849 | 2100 | 9.9 | 1.5 | 0.9 |
| example 57 | 1025 | 2200 | 17.4 | 1.5 | 0.5 |
| example 58 | 913 | 230 | 7.3 | 1.9 | 5.8 |
| example 59 | 882 | 160 | 8.2 | 1.3 | 5.7 |
| example 60 | 992 | 2040 | 15.7 | 1.7 | 0.6 |
| example 61 | 611 | 1840 | 9.4 | 1.6 | 0.8 |
| example 62 | 828 | 1760 | 5.2 | 1.1 | 0.9 |
| example 63 | 43 | 990 | 11.6 | 2.0 | 4.8 |
| example 64 | 762 | 2800 | 6.5 | 1.9 | 1.3 |
| example 65 | 830 | 3100 | 9.4 | 2.1 | 1.1 |
| example 66 | 1018 | 330 | 15.4 | 1.5 | 5.3 |
| example 67 | 873 | 410 | 12.2 | 1.4 | 5.5 |
| example 68 | 755 | 2890 | 11.4 | 1.7 | 0.9 |
| example 69 | 923 | 3060 | 12.8 | 1.9 | 0.8 |
| example 70 | 789 | 2360 | 7.9 | 2.0 | 1.1 |
| example 71 | 803 | 2220 | 4.7 | 1.4 | 1.2 |
| example 72 | 1021 | 2460 | 15.1 | 1.5 | 0.7 |
| example 73 | 1013 | 2590 | 15.8 | 1.5 | 0.9 |
| example 74 | 994 | 2550 | 15.8 | 1.7 | 0.6 |
| example 75 | 998 | 2310 | 15.0 | 2.0 | 0.9 |
| example 76 | 970 | 2470 | 15.4 | 2.1 | 1.1 |
| example 77 | 990 | 2800 | 14.7 | 1.5 | 1.2 |
| example 78 | 980 | 2670 | 14.9 | 1.3 | 0 |
| example 79 | 996 | 3300 | 15.5 | 1.8 | 0.9 |
| example 80 | 1009 | 4830 | 16.3 | 1.9 | 0.5 |
| example 81 | 1012 | 4990 | 16.0 | 1.9 | 0.4 |
| example 82 | 995 | 4650 | 14.7 | 1.9 | 0.7 |
| example 83 | 990 | 4260 | 14.9 | 1.8 | 0.5 |
| example 84 | 834 | 5670 | 12.3 | 2.0 | 1.4 |
| example 85 | 976 | 3240 | 15.2 | 2.1 | 1.1 |
| example 86 | 984 | 3440 | 15.1 | 2.1 | 1.2 |
| example 87 | 980 | 3660 | 15.8 | 2.2 | 1.4 |
| example 88 | 787 | 5530 | 10.0 | 2.3 | 1.6 |
| example 89 | 723 | 3010 | 14.0 | 2.1 | 1.3 |
| example 90 | 840 | 5780 | 6.7 | 1.9 | 0.4 |
| example 91 | 958 | 5980 | 15.2 | 1.5 | 1.1 |
| example 92 | 963 | 5970 | 15.4 | 1.5 | 1.1 |

The invention claimed is:

1. A sorbent for sorption removal of cytokines and bacterial endotoxins from fluids selected from the group comprising body fluids, and aqueous protein solutions that contain inorganic salts, characterized in that the sorbent has specific surface area of 610 to 1025 m²/g, sorption capacity with respect to bacterial endotoxins of 170 to 5990 EU/mL, sorption capacity with respect to myoglobin of 3.4 to 17.2 mg/g, swelling by weight of 1.1 to 2.3 mL/g, hemolytic activity of 0% to 5.6%.

2. The sorbent of claim 1, characterized in that the sorbent consists of pellets having sizes ranging from 1 μm to 1.5 mm.

3. The sorbent of claim 1, characterized in that the sorbent consists of pellets having sizes ranging from 300 μm to 1.0 mm.

4. The sorbent of claim 1, characterized in that the aqueous protein solutions further contains organic compounds.

5. The sorbent of claim 2, characterized in that the sorbent consists of pellets having sizes ranging from 50 μm to 1000 μm (1 mm).

6. The sorbent of claim 5, characterized in that the sorbent consists of pellets having sizes ranging from 100 μm to 800 μm.

7. The sorbent of claim 3, characterized in that the sorbent consists of pellets having sizes ranging from 300 μm to 800 μm.

8. The sorbent of claim 7, characterized in that the sorbent consists of pellets having sizes ranging from 300 μm to 500 μm.

* * * * *